United States Patent [19]

Smith et al.

[11] 4,272,445
[45] Jun. 9, 1981

[54] PROCESS FOR PREPARING ACTIVE COMPOUNDS

[75] Inventors: Paul Smith, Hoddesdon; Frederick Cassidy, Harlow, both of England

[73] Assignee: Beecham Group Limited, England

[21] Appl. No.: 907,778

[22] Filed: May 19, 1978

[30] Foreign Application Priority Data

May 25, 1977 [GB] United Kingdom ............... 21961/77

[51] Int. Cl.³ .............................................. C07J 1/00
[52] U.S. Cl. ............................. 260/397.4; 260/397.5; 260/239.55 C; 260/239.5
[58] Field of Search ......................... 260/397.4, 397.45

[56] References Cited

U.S. PATENT DOCUMENTS 3,049,555  8/1962  Tyner ................................ 260/397.4

FOREIGN PATENT DOCUMENTS 911428  11/1962  United Kingdom .................. 260/397.4
922511   4/1963  United Kingdom .................. 260/397.4

OTHER PUBLICATIONS

"Steroid Reactions" (1963) by Djerassi, pp. 48 and 49.
Organic Reactions in Steroid Chemistry, vol. 1, (1974) by Fried et al. pp. 393 and 394.

Primary Examiner—Elbert L. Roberts
Attorney, Agent, or Firm—Jacobs & Jacobs

[57] ABSTRACT

A process for the preparation of a compound of the formula (A):

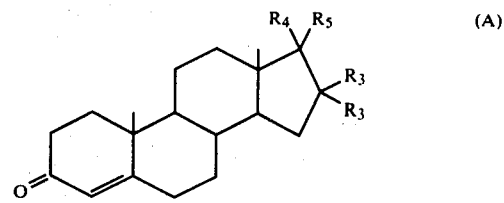

wherein: $R_3$ is a $C_{1-5}$ alkyl group, a $C_{3-6}$ alkenyl group, a $C_{3-6}$ cycloalkyl group or an alkylphenyl group in which the alkyl moiety contains 1 to 3 carbon atoms and the phenyl moiety is optionally substituted; $R_4$ is a hydroxyl group, or a group $OR_6$ wherein $R_6$ is a $C_{2-7}$ acyl group, a $C_{1-4}$ alkyl group, or an optionally substituted benzyl group; $R_5$ is hydrogen or a $C_{1-5}$ alkyl group; or $R_4$ and $R_5$ together with the carbon atom to which they are joined represent a carbonyl group; which process comprises the reaction of a compound of the formula (C):

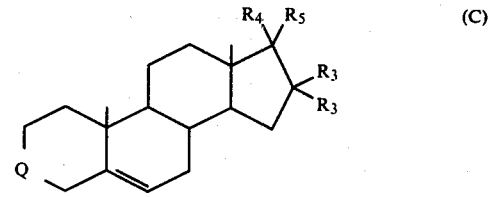

wherein Q is a carbonyl group protected by a reagent capable of selectively protecting the 3-carbonyl of androstenedione, and $R_3$, $R_4$ and $R_5$ are as defined in formula (A), to generate an unprotected carbonyl group in place of the protected carbonyl group Q.

This process has advantages over the known process for the preparation of compounds of formula (A).

7 Claims, No Drawings

PROCESS FOR PREPARING ACTIVE COMPOUNDS

This invention relates to a process for preparing active compounds. More specifically this invention relates to an improved process for the preparation of a class of steroids known to have useful properties in the treatment of androgen dependent skin disorders.

In W. German Offlegungsschrift No. 2610497, the disclosure of which is incorporated into this application by reference, it is disclosed inter alia that compounds of the formula (A):

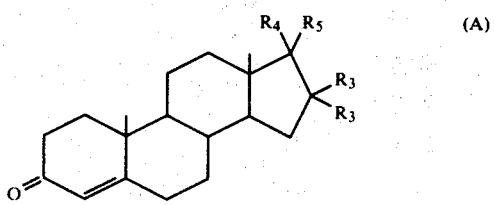

wherein: $R_3$ is a $C_{1-5}$ alkyl group, a $C_{3-6}$ alkenyl group, a $C_{3-6}$ cycloalkyl group or an alkylphenyl group in which the alkyl moiety contains 1 to 3 carbon atoms and the phenyl moiety is optionally substituted; $R_4$ is a hydroxyl group, or a group $OR_6$ wherein $R_6$ is a $C_{2-7}$ acyl group, a $C_{1-4}$ alkyl group or an optionally substituted benzyl group; $R_5$ is hydrogen or a $C_{1-5}$ alkyl group; or $R_4$ and $R_5$ together with the carbon atom to which they are joined represent a carbonyl group; maybe used in the treatment of androgen dependent skin disorders.

The Offenlegungsschrift also discloses a process for the preparation of compounds of the formula (A) starting from testosterone, the final stage of which is the reaction of a compound of formula (B):

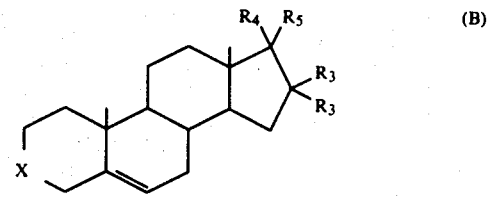

wherein X is a protected carbonyl group and $R_3$, $R_4$ and $R_5$ are as defined in formula (A), to generate an unprotected carbonyl group in place of the protected carbonyl group X. Suitable protecting reagents for the X carbonyl are stated to be ketals and thioketals.

It has now been discovered that the use of a certain class of protecting reagents not specifically disclosed in the Offenlegungsschrift enables the compounds of the formula (A) to be prepared from androstenedione in a preparative sequence which involves fewer stages, and can give improved yields.

Accordingly, in its broadest aspect, the present invention provides a process for the preparation of a compound of the formula (A) as hereinbefore defined, which process comprises the reaction of a compound of the formula (C):

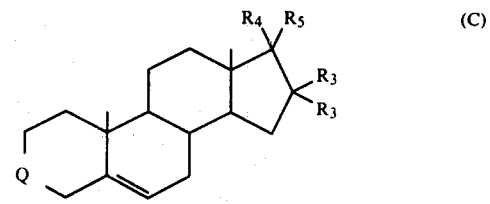

wherein Q is a carbonyl group protected by a reagent capable of selectively protecting the 3-carbonyl of androstenedione, and $R_3$, $R_4$ and $R_5$ are as defined in formula (A), to generate an unprotected carbonyl group in place of the protected carbonyl group Q.

It has been found that suitable protecting reagents include those capable of forming enol ethers and enolthio ethers at the 3-carbonyl of androstenedione. Thus it will be realised that suitably the compound of formula (C) used in the process of the invention will be of formula (D):

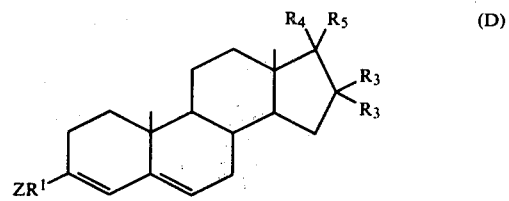

wherein $R^1$ is the organic residue of a compound capable of forming an enol ether or enol thio ether at the 3-carbonyl group of androstenedione, and Z is oxygen or sulphur.

Suitable examples of $R^1$ include $C_{1-6}$ alkyl groups, such as ethyl; phenyl; phenyl $C_{1-3}$ alkyl groups, such as benzyl; and $C_{5-6}$ cycloalkyl groups. Preferably Z is oxygen.

One particularly suitably value for $Z-R^1$ in formula (D) is $O-CH_2-CH_3$.

Other suitable protected carbonyl groups Q include enol esters, such as enol $C_{1-6}$ alkyl esters, for example the enol acetate; and the enol benzoate ester.

The deprotection reaction may be carried out in conventional manner for removing carbonyl protecting reagents, for example by hydrolysis in the presence of a suitable catalyst such as an acid.

More specifically, enol ether protecting groups may suitably be removed by treatment with dilute aqueous acid in the presence of an organic solvent such as ether or an alcohol.

Enol thioether protecting groups maybe removed in a generally similar manner to enol ether protecting groups, but more rigorous conditions may be necessary.

After this de-protection reaction, if desired when $R_4$ and $R_5$ do not form a carbonyl group the group $R_4$ may be varied by conventional methods. For example, compounds of the formula (A) wherein $R_4$ is an acylated or etherified hydroxyl group may be prepared by conventional acylation of etherification of compounds of the formula (A) wherein $R_4$ is a hydroxyl group. Such reactions include reaction of the hydroxyl moiety with acyl chlorides or acyl anhydrides such as acetyl chloride or acetic anhydride under anhydrous conditions to give acyl derivatives, and reaction of a sodium salt of the hydroxyl moiety with an alkyl halide to given an etherified derivative.

The compounds of the formula (C) may themselves be prepared by a process which comprises substituting a compound of the formula (E):

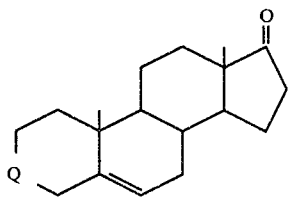
(E)

at the 16 position with the required groups $R_3$, and thereafter if desired converting the 17-carbonyl group to other groups $R_4$ and $R_5$ by conventional methods; Q, $R_3$, $R_4$ and $R_5$ are as defined in formula (C). (Less desirably, the 16-mono substituted intermediates in this reaction may first be isolated, and then further substituted at the 16 position.)

The substitution reaction may suitable be carried out by reacting the chosen compound of the formula (E) with a compound $R_3Y$ in the presence of a strong base of low nucleophilicity. Suitably Y is a readily displaceable group, such as a halide, tosylate, mesylate or azide, the base is a hydride such as sodium hydride, and the reaction is carried out in anhydrous conditions.

The optional conversion of the 17-carbonyl group into other groups $R_4$ and $R_5$ may be carried out by the usual conventional methods. For example, compounds wherein $R_4$ is a hydroxyl group and $R_5$ is either hydrogen or a $C_{1-5}$ alkyl group may be formed from the corresponding 17-carbonyl compound by reduction or by reaction with a $C_{1-5}$ alkyl Grignard reagent or a $C_{1-5}$ alkyl metallic complex (suitably a $C_{1-5}$ alkyl lithium complex) respectively. The reduction may suitably be carried out using lithium aluminium hydride or sodium borohydride. Thereafer, if desired, the thus formed $R_4$ hydroxyl group may itself be acylated or etherified to give another group $R_4$ by methods previously described.

It will be appreciated that certain of the conditions used in these optional reactions may result in subsequent deprotection of the protected 3-carbonyl group Q to produce the desired final product of formula (A).

The compounds of the formual (E) may be prepared by a process which comprises the selective protection of androstenedione at its 3-carbonyl.

This reaction may be carried out in conventional manner depending on the nature of the protecting reagent.

For example enol ether protection may be carried out by reacting the androstenedione with an ortho ester, such as tri-methyl or tri-ethyl ortho formate, in the presence of an acid catalyst, such as p-toluenesulphonic acid. The reaction is suitably carried out in an organic solvent such as benzene or the like, at a suitable temperature between room temperature and reflux.

For the preparation of methyl or ethyl enol ethers, tri-methyl or tri-ethyl ortho formate may be used. For the preparation of other enol ethers it generally more suitable to use either of these two ortho formates in the presence of the relevant alcohol $R^1OH$.

Enol thio ether protection may generally be effected by reacting the androstenedione with the necessary thiol in the presence of an acid catalyst.

Enol ester protection may generally be effected by reacting the androstenedione with a reactive acylating derivative of the appropriate acid.

Many of the compounds of the formula (E) are known compounds.

Androstenedione is commercially available,

From the aforesaid description, it can be seen that the invention provides a preparative route for compounds of the formula (A) starting from androstenedione, which may be represented schematically:

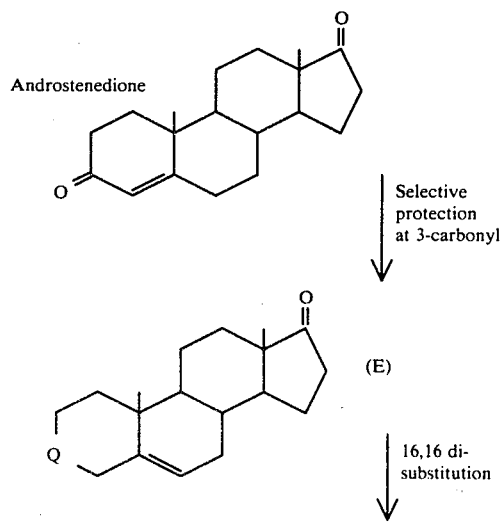

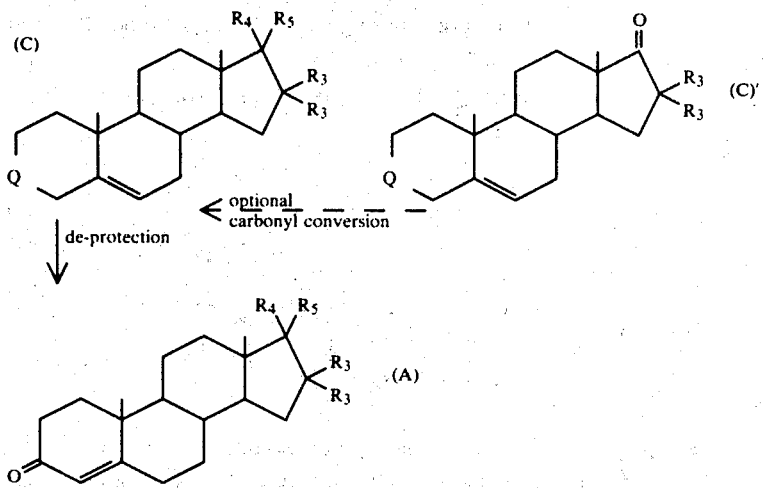

This preparative route represents an important embodiment of the invention.

It will be appreciated that the process of the invention will be particularly suitable for the preparation of compounds of the formula (A) stated to be suitable and preferred compounds in the Offenlegungsschrift. Thus in the process, and also of course in the compounds of formula (C):

(i) Suitable examples of $R_3$ include the following groups: methyl, ethyl, propyl, cyclopropyl, cyclopentyl, cyclohexyl, benzyl and phenylethyl. The phenyl moieties of the benzyl and phenylethyl groups may be substituted by, for example a $C_{1-4}$ alkyl, halogen or nitro group. $R_3$ may also suitably be an allyl or butenyl group. Preferably $R_3$ is a methyl, ethyl or n- or iso-propyl group, most preferably a methyl group.

(ii) $R_4$ is most suitably a hydroxyl group. However, when $R_4$ is a group $OR_6$, suitable examples of $R_6$ include the following groups: acetyl, n- and iso-propionyl, n-, sec- and tert-butyryl, caproyl, heptanoyl, methyl, ethyl, n- and iso-propyl and n-, sec- and tert-bytyl, and benzyl. The phenyl moiety of the benzyl group may be substituted by, for example, a $C_{1-4}$ alkyl, halogen or nitro group. Suitably $R_4$ has the $\beta$ configuration.

(iii) Suitable examples of $R_5$ include hydrogen, and the methyl, ethyl, n- and iso-propyl, and n-butyl groups. Preferably $R_5$ is hydrogen or a methyl group, most preferably hydrogen.

For example, suitably the process of the invention is adapted for the preparation of a compound of formula (F)

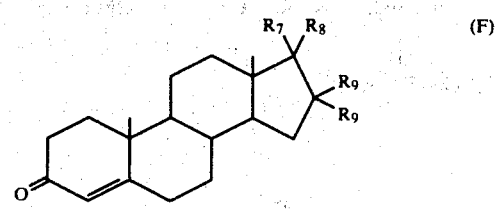

wherein: $R_7$ is a hydroxyl group, or a hydroxy group acylated by a $C_{2-7}$ acyl group; $R_8$ is hydrogen, or a $C_{1-4}$ alkyl group; or $R_7$ and $R_8$ taken together with the carbon atom to which they are joined form a carbonyl group; and $R_9$ is a $C_{1-3}$ alkyl group.

In formula (F) when $R_7$ is a hydroxyl group acylated by a $C_{2-7}$ acyl group, it is suitably an acetoxy, n- or iso-propionoxy, caproyloxy or heptanoyloxy group.

$R_7$ is preferably a hydroxyl group.

It is preferred that $R_7$ has the $\beta$ configuration.

$R_8$ is suitably hydrogen or methyl, most suitably hydrogen.

$R_9$ is suitably a methyl or ethyl group, preferably a methyl group.

Within the compounds of the formula (F), a particularly preferred class of compounds which can be prepared by the process of the invention are those of the formula (G):

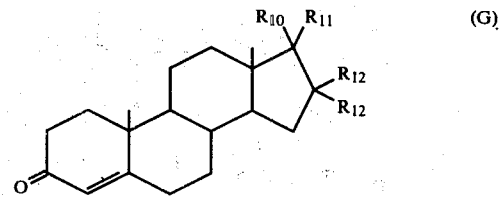

wherein: $R_{10}$ is a hydroxyl group or a hydroxyl group acylated by a $C_{2-7}$ acyl group; $R_{11}$ is hydrogen, or a methyl or ethyl group; or $R_{10}$ and $R_{11}$ taken together with the carbon atom to which they are joined represent a carbonyl group; and $R_{12}$ is a methyl or ethyl group.

Examples of groups $R_{10}$ include hydroxyl, acetoxy, n- or iso-propionyloxy, caproyloxy and heptanoyloxy groups.

Preferably $R_{10}$ is a hydroxyl group, and normally the group $R_{10}$ will be in the $\beta$ configuration.

Preferably $R_{11}$ is hydrogen, or a methyl group, or $R_{10}$ and $R_{11}$ taken together with the carbon atom to which they are joined represent a carbonyl group. More suitably $R_{11}$ is a hydrogen atom.

Preferably $R_{12}$ is a methyl group.

In a preferred embodiment the process of the invention is adapted for the preparation of androst-4-en-16,16-dimethyl-17$\beta$-ol-3-one, a compound of particularly useful properties as is clear from the Offenlegungsschrift.

It will be realised that when the process of the invention is adapted for the preparation of a compound of the formula (F) or (G) as hereinbefore defined, then the corresponding intermediate of formula (C) will be of formula (H) or (I) respectively:

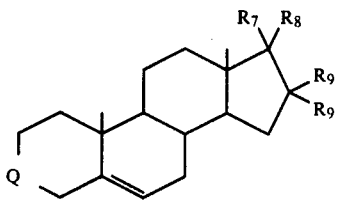

OR

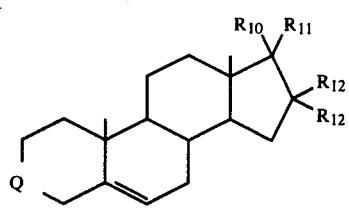

wherein the variable groups are as defined in formula (F) or (G) respectively.

Suitable and preferred examples of the variables in formula (H) and (I) are as hereinbefore described.

The pharmaceutical use of compounds of the formula (A) is described in the Offenlegungsschrift.

It is believed that compounds of the formula (C) which are useful intermediates are novel, and as such form an important part of this invention.

The following Examples illustrate the process of the invention:

EXAMPLE 1

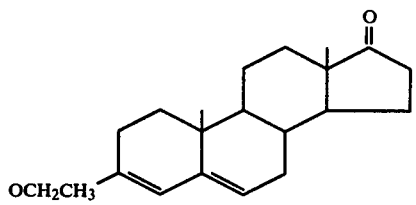

Androstenedione (5 g.) was dissolved in dry benzene (20 ml). Triethyl orthoformate (6 ml) was added, followed by p-toluenesulphonic acid (250 mg) and the solution left at room temperature for ten minutes. The benzene solution was washed with aqueous sodium hydroxide (10%), followed by water, dried (anhydrous Na₂SO₄) and evaporated under reduced pressure to give a pale yellow solid (5.5 g.). This solid was recrystallized from ethanol to give 3-ethoxy-androsta-3,5-dien-17-one (4.3 g.) as white needles, m.p. 146°–149°.

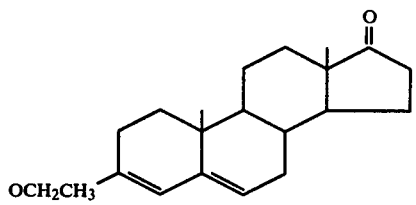

Androstenedione (10 g.) was dissolved in propan-2-ol (500 ml). Triethyl orthoformate (7.15 ml) was added, followed by p-toluenesulphonic acid (250 mg) and the solution refluxed for fifteen minutes. A few drops of pyridine were added and the solution evaporated under reduced pressure to give a pale yellow solid. This was recrystallised from methanol to give 3-iso-propoxy-androsta-3,5-dien-17-one (8.0 g) as white crystals, M.p. 147°–151°.

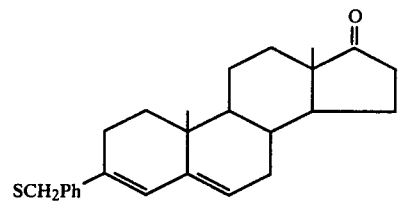

Androstenedione (5 g) was dissolved in benzene (150 ml) and ethanol (12 ml). Benzyl mercaptan (5 g) was added, followed by pyridine hydrochloride (150 mg) and the solution refluxed for three hours [according to the method of C. Djerassi et al JACS (1951) 73, 1528]. After cooling, the solution was diluted with ether, washed with 10% Na₂CO₃, dried (anhydrous Na₂SO₄) and evaporated under reduced pressure to give a pale yellow oily solid. This was recrystallised from methanol to give Δ⁴-androstene-3,17-dione-3-benzylthioenol ether (3 g) as white needles, M.p. 175°–178°.

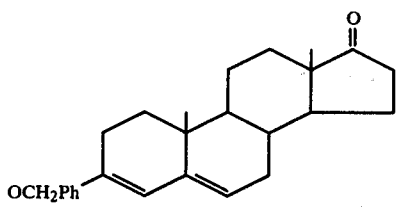

Androstenedione (5 g) was dissolved in dry benzene (100 ml). Triethyl orthoformate (3.25 ml) was added, followed by p-toluenesulphonic acid (20 mg) and the solution heated at 50° for 45 minutes. Benzyl alcohol (7.5 ml) and benzene (150 ml) were then added and the solution distilled until 150 ml of distillate had been collected. A few drops of pyridine were added and the solution evaporated under reduced pressure to give a yellow solid. This solid was recrystallised from ethanol to give 3-benzyloxy-androsta-3,5-dien-17-one (5.4 g) as white needles, M.p. 172°–178°.

In a similar manner the following were prepared:

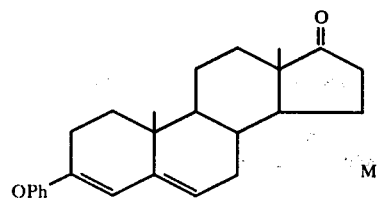

M.p. 135–140°

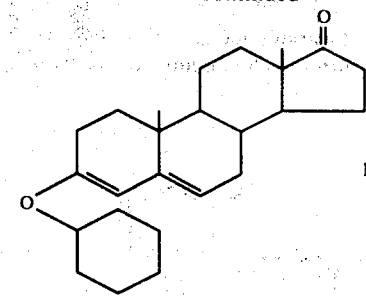

M.p. 157-160°

EXAMPLE 2

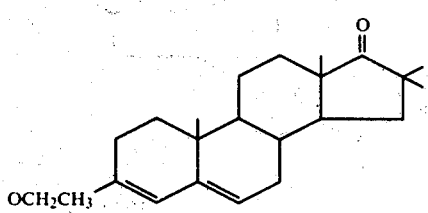 (a)

3-Ethoxy-androsta-3,5-dien-17-one (2 g.) was dissolved in dry tetrahydrofuran (25 ml). Sodium hydride (0.79 g.) was added, followed by methyl iodide (1.8 ml), and the reaction mixture was refluxed, with stirring, for 4 hours. The tetrahydrofuran was evaporated under reduced pressure and the residue partitioned between ether and water. The ether layer was washed again with water, dried (anhydrous Na₂SO₄) and evaporated to give a white solid (2.2 g.). The solid was recrystallised from methanol to give 16,16-dimethyl-3-ethoxy-androsta-3,5-dien-17-one (1.8 g.) as white needles, m.p. 133°-137°.

(b) The following were prepared in a similar manner:

| Compound | Rexⁿ Solvent | M pt | % yield |
|---|---|---|---|
| (OCH(CH₃)₂) | MeOH | 119-123 | 46 |
| (O-cyclohexyl) | EtOH | 155-160 | 71 |
| (OCH₂Ph) | CH₂Cl₂/60-80 petrol | 212-215 | 60 |
| (OPh) | EtOH | 151-155 | 64 |
| (SCH₂Ph) | EtOH | 180-186 | 75 |

EXAMPLE 3

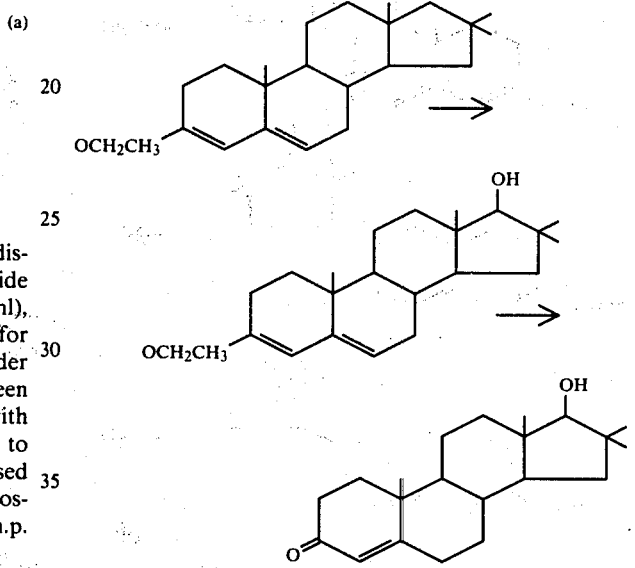 (a)

16,16-Dimethyl-3-ethoxy-androsta-3,5-dien-17-one (5 g) was added to ether (60 ml) containing lithium aluminium hydride (200 mg) and the mixture stirred for 30 minutes at room temperature. A few drops of water were then added, followed by 5 N HCl and ether (60 ml). The two phases were then stirred together rapidly for 20 minutes, separated and the organic layer washed with water, dried (anhydrous Na₂SO₄) and evaporated under reduced pressure to give a white solid. This solid was recrystallised from ethyl acetate/petrol (60°-80°) to give androst-4-en-16,16-dimethyl-17β-ol-3-one (3 g) as white needles, m.p. 174°-175°.

(b) Androst-4-en-16,16-dimethyl-17β-ol-3-one was also prepared from the following enol ethers in a similar manner to method in example 3(a):

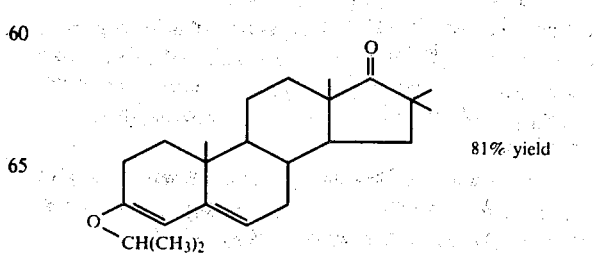

81% yield

11
-continued

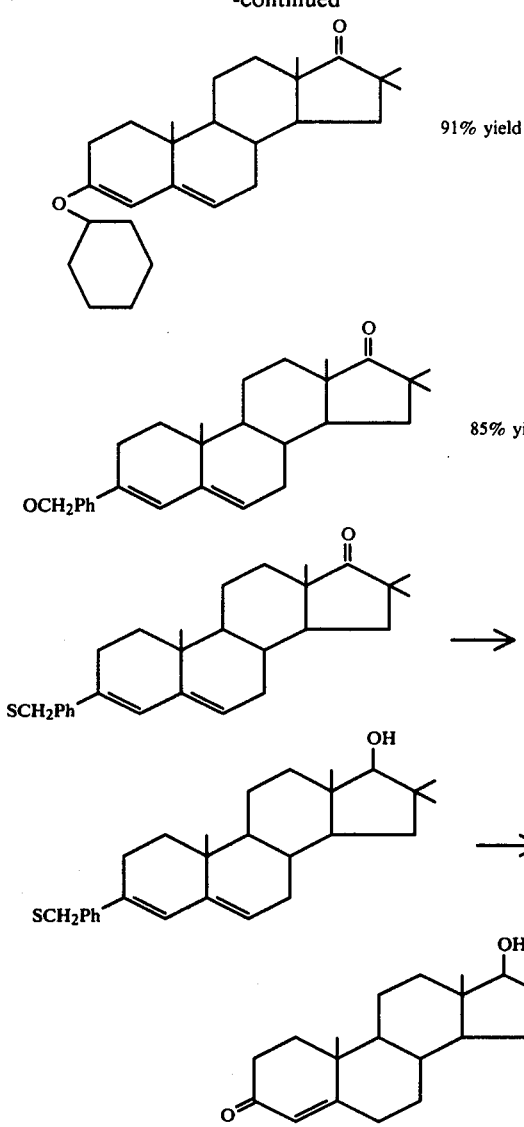

3-Benzylthio-16,16-dimethylandrosta-3,5(6)-dien-17-one (500 mg) was added to ether (50 ml) containing lithium aluminium hydride (100 mg) and the mixture stirred at room temperature for 4 hours. A few drops of water were added, followed by 5 N HCl. The ether layer was separated, evaporated under reduced pressure and the residue dissolved in methanol (45 ml)/water (5 ml) containing conc. HCl (0.25 ml). The solution was refluxed for 30 minutes and then most of the methanol was removed under reduced pressure and the residue partioned between ether and water. The ether layer was washed with water, dried (anhydrous $Na_2SO_4$) and evaporated under reduced pressure to give a yellow oily solid. This solid was recrystallised from ethyl acetate/petrol (60°–80°) to give androst-4-en-16,16-dimethyl-17β-ol-3-one (270 mg) as white needles, m.p. 173°–175°.

Androst-4-en-16,16-dimethyl-17β-ol-3-one was also prepared from 3-phenoxy-16,16-dimethyl-androsta-3,5-dien-17-one in a similar manner (84% yield).

12
EXAMPLE 4

This example illustrates the use of sodium borohydride in place of lithium aluminium hydride as used in Example 3(a).

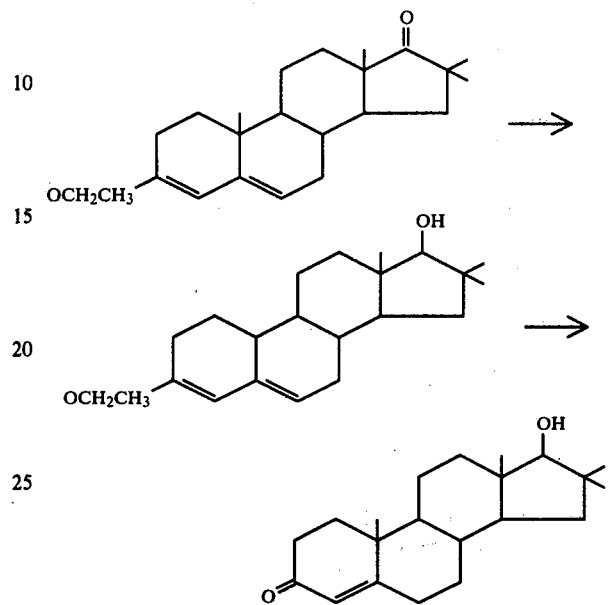

16,16-Dimethyl-3-ethoxy androsta-3,5-dien-17-one (342 mg) was dissolved in ethanol (10 ml) and sodium borohydride (170 mg) added. The reaction mixture was heated at 35° C. for 24 hours. Dilute hydrochloric acid (5 N) was added until the reaction mixture was strongly acidic (approx. pH=1). Aqueous sodium bicarbonate (saturated) was added to neutralise the reaction mixture which was then partially evaporated under reduced pressure in order to remove most of the ethanol. The remaining mixture was extracted with methylene chloride and the organic layer washed three times with water, dried ($Na_2SO_4$) and evaporated to give a white solid (310 mg). The solid was re-crystallised from ethyl acetate/petrol (60°–80°) to give androst-4-en-16,16-dimethyl-17β-ol-3-one (250 mg) as white needles, m.p. 170°–172°.

What we claim is:

1. The process for the preparation of a 16,16-disubstituted androst-4-en-3 one of the formula:

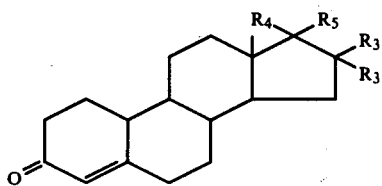

wherein $R_4$ and $R_5$ are together oxo or $R_4$ is hydroxy, and $R_5$ is hydrogen or alkyl of 1 to 5 carbon atoms, and each $R_3$ is alkyl of 1 to 5 carbon atoms, which comprises (a) converting androst-4-ene-3,17-dione to an androsta-3,5(6)-dien-17-one of the formula:

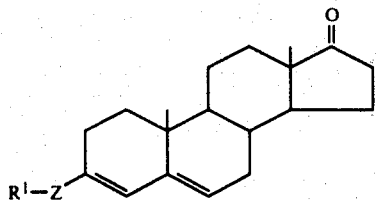

wherein Z is oxygen or sulfur and $R^1$ is alkyl of 1 to 6 carbon atoms, phenyl, phenylalkyl of 7 to 9 carbon atoms or cycloalkyl of 5 or 6 carbon atoms by treatment with a reagent operable to effect selective enol ether or enol thioether formation, (b) treating said androsta-3,5(6)-dien-17-one with $R_3Y$ wherein $R_3$ is as defined above and Y is a halide, tosylate, mesylate or azide in the presence of a strong base of low nucleophilicity to yield a 16,16-disubstituted androsta-3,5(6)-dien-17-one of the formula:

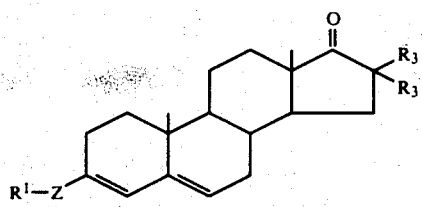

wherein $R^1$, Z and $R_3$ are as defined above, (c)
  (i) when $R_4$ and $R_5$ are to be other than oxo and $R_5$ is to be hydrogen, reducing said 16,16-disubstituted androsta-3,5(6)-dien-17-one to produce the corresponding 16,16-disubstituted androsta-3,5(6)-dien-17-ol, or
  (ii) when $R_4$ and $R_5$ are to be other than oxo and $R_4$ is to be alkyl, alkylating said 16,16-di-substituted androsta-3,5(6)-dien-17-one to produce the corresponding 16,16-disubstituted 17-alkylandrosta-3,5(6)-dien-17-ol, and (d) hydrolyzing said 16,16 disubstituted androsta-3,5(6)-dien-17-one, said 16,16-disubstituted androsta-3,5(6)-dien-17-ol or said 16,16-disubstituted 17-alkylandrosta-3,5(6)-dien-17-ol with aqueous acid to yield said 16,16-disubstituted androst-4-en-3-one.

2. A process according to claim 1, wherein Z is oxygen.

3. A process according to claim 2 wherein $R^1$ is ethyl.

4. A process according to claim 1 wherein $R_3$ is methyl, $R_4$ is hydroxyl and $R_5$ is hydrogen.

5. A process according to claim 4 wherein Z is oxygen and $R^1$ is ethyl.

6. The process according to claim 1 wherein androst-4-en-3,17-dione is treated with ethyl orthoformate to yield 3-ethoxyandrosta-3,5(6)-dien-17-one.

7. The process according to claim 6 wherein said 3-ethoxyandrosta-3,5(6)-dien-17-one is treated with methyl iodide in the presence of sodium hydride.

* * * * *